United States Patent [19]

Wenke et al.

[11] Patent Number: 5,486,619
[45] Date of Patent: Jan. 23, 1996

[54] METHOD OF PRODUCING DAI FROM DOPA, USING ONE REACTION VESSEL

[75] Inventors: Gottfried Wenke, Woodbridge; Yuh-Guo Pan, Stamford; Mu-Ill Lim, Trumbull; Linas Stasaitis, Fairfield, all of Conn.

[73] Assignee: Clairol, Inc., New York, N.Y.

[21] Appl. No.: 235,763

[22] Filed: Apr. 29, 1994

[51] Int. Cl.$^6$ .................................................. C07D 209/08
[52] U.S. Cl. ............................................. 548/508; 548/469
[58] Field of Search ...................................... 548/508, 469

[56] References Cited

U.S. PATENT DOCUMENTS

| 4,822,375 | 4/1989 | Lang et al. | 8/423 |
| 5,262,546 | 11/1993 | Pan et al. | 548/508 |
| 5,279,618 | 1/1994 | Prota et al. | 8/406 |

*Primary Examiner*—Jacqueline Haley
*Attorney, Agent, or Firm*—Anthony M. Santini

[57] ABSTRACT

A method of producing and isolating 5,6-diacetoxyindole (DAI) in a single reaction vessel comprising the following steps:

(a) preparing a first solution comprising dopa, water and a solubilizing agent selected from the group consisting of an acid having a $pk_a$ value equal to or less than 4 and a first base having a $pk_b$ value equal to or greater than 10;

(b) preparing a second solution comprising an oxidant, a buffer and water;

(c) mixing the first and second solutions to form a combined solution which is rendered oxygen-free and has a pH of from about 6 to about 9;

(d) stirring the combined solution in an inert atmosphere until 5,6-dihydroxyindole (DHI) is substantially completely formed;

(e) adding a derivatizing agent and a second base to the combined solution to form a final solution;

(f) stirring the final solution until the DHI is substantially fully consumed;

(g) cooling the final solution to precipitate DAI;

(h) isolating the precipitated DAI.

20 Claims, No Drawings

METHOD OF PRODUCING DAI FROM DOPA, USING ONE REACTION VESSEL

BACKGROUND OF THE INVENTION

This invention relates to a method for producing and isolating 5,6-diacetoxyindole (DAI) in a single reaction vessel using 3,4-dihydroxyphenylalanine (dopa) as a starting material.

DAI is well known as a stable melanin precursor that is useful as a hair dye. However, prior known methods of producing and isolating DAI have disadvantages that have discouraged its use on an industrial scale. Such methods typically involve multiple steps that must be performed in several reaction vessels. As a result, those methods for producing DAI are costly and time-consuming.

For example, Beer, R. J. S. et. al., *J. Chem. Soc.*, 2223–26 (1948) discloses the production of DAI by reductive cyclization of 4,5-diacetoxy-2,β-dinitrostyrene (a material that itself must first be synthesized) with iron in acetic acid and absolute alcohol. The reaction mixture was filtered and the filtrate was diluted with water, basified with sodium hydrogen carbonate, and extracted five times with ether. The mixture was evaporated to give a viscous gum that partially crystallized when placed in a vacuum. The DAI crystals were purified by being extracted several times with hot light petroleum-containing benzene.

Similarly, Murphy, Bryan P., *J. Org. Chem.*, 50, 5873–75 (1985), discloses a multistep procedure which, using piperonal as a starting material, yields DAI only after acetylation of the resulting mixture, removal of the solvent in vacuo, and HPLC purification. See also, for example, Burton, H. et. al., *J. Chem. Soc.*, 78–9 (1949); Burton, H. et. al., *J. Chem. Soc.*, 1062–64 (1950); Ek, Arvid et. al., *J. Amer. Chem. Soc.*, 76, 5579–88 (1954); Shaw, Kenneth N. F. et. al., *Biochem. Prep.*, 9, 12–21 (1962); and Suvorov, N. N et. al., *Zh. Obshch. Khim.*, 30, 3118–23 (1960).

SUMMARY OF THE INVENTION

The present invention relates to a method for producing and isolating DAI in a single reaction vessel, using dopa as a starting material. The method comprises preparing a first solution of dopa, a solubilizing agent and water; and preparing a second solution of an oxidant, buffer and water. The two solutions are then mixed to form a combined solution which is rendered oxygen-free. Preferably, this is achieved by bubbling an inert gas (nitrogen or argon) through the combined solution. Alternatively, the first and second solutions can individually be contacted with the inert gas to render each one oxygen-free, to ultimately result in a combined oxygen-free solution. The combined solution is then stirred in an inert atmosphere, whereupon 5,6-dihydroxyindole (DHI) is formed as an intermediate. It is critically important that the combined solution is ultimately oxygen-free, and that the stirring takes place in an inert atmosphere. Otherwise, if DHI is exposed to oxygen, it will polymerize. Consequently, the yield of DAI will be substantially decreased and, potentially, DAI will not be formed at all.

The stirring step continues until DHI is substantially completely formed. Then, a derivatizing agent and a base are simultaneously or sequentially added to the combined solution to form a final solution. The final solution is then stirred until substantially all of the DHI is consumed by the reaction. DAI is then precipitated by cooling the final solution, and the precipitated DAI is then isolated by any known method, such as filtration.

The yield of DAI using this method is surprisingly and unexpectedly high, particularly in view of the absence of a DAI purification step. It has also been found that, when the temperature of the combined solution is raised to about 30° C. to about 70° C., higher yields of DHI (and consequently DAI) are produced than when the reaction is performed at ambient temperature.

It is therefore an object of this invention to provide an inexpensive and time-efficient method for producing and isolating DAI.

It is also an object of this invention to provide a straightforward method, in which only one reaction vessel is used, for producing and isolating DAI.

It is further an object of this invention to provide a method for producing and isolating a good yield of DAI.

Accordingly, applicants have surprisingly found a method for producing and isolating DAI in one reaction vessel, using dopa as a starting material.

DETAILED DESCRIPTION OF THE INVENTION

The method of the present invention comprises an initial step in which a first aqueous solution comprising dopa, a solubilizing agent and water is prepared. Since, by itself, dopa is not water-soluble, the purpose of the initial step is to solubilize dopa with the solubilizing agent. The amount of dopa used can be varied according to the quantity of DAI end product that is desired. The range of dopa in the first solution is from about 1 mmol./100 ml. to about 50 mmol./100 ml.; preferably, from about 5 mmol./100 ml. to about 15 mmol./100 ml. The solubilizing agent can be any acid or base which, if an acid, will protonate (i.e. positively charge) the dopa compound or, if a base, will de-protonate (i.e. negatively charge) the dopa compound. Suitable solubilizing agents are acids having a $pk_a$ value equal to or less than 4, and bases having a $Pk_b$ value equal to or greater than 10. Some of the preferred acids that can be used are hydrochloric acid and phosphoric acid. Some of the preferred bases that can be used are sodium hydroxide and potassium hydroxide. The amount of solubilizing agent used will be a function of the type of solubilizing agent used as well as the amount of dopa used. In general, the molar amount of solubilizing agent used should be at least equivalent to the molar amount of dopa used. The amount of water added to the solubilized dopa should be from about 5 to about 10 ml/mmol dopa.

Next, a second aqueous solution comprising an oxidant, a buffer and water is prepared for addition to the first solution to form a combined solution which will ultimately react and convert the dopa to DHI. The oxidants that can be used in accordance with this invention are water-soluble ferricyanide salts such as, for example, potassium ferricyanide, sodium ferricyanide and ammonium ferricyanide. The amount of oxidant used should be sufficient to convert substantially all of the dopa to DHI. This requires about 3 to about 4 molar equivalents of dopa.

Some of the buffers that can be used are selected from the group consisting of sodium bicarbonate, potassium bicarbonate, phosphate, borate and aminic buffers, such as Trizma®. The amount of buffer used should be sufficient to maintain the pH of the combined solution at about pH 6 to about pH 9 during the dopa oxidation reaction. However, the buffer must not react with the oxidant before being combined with the dopa solution. In the absence of a buffer, the solution could become increasingly acidic since acid is liberated during the conversion of dopa to DHI.

The minimum amount of water that should be used in the second solution is the amount necessary to dissolve the oxidant and the buffer. Preferably, the amount of water added to the second solution will be such that the concentration of dopa in the combined solution is about 0.1% to about 5%, most preferably about 0.5% to about 1.5 %.

The second solution is then mixed with the first solution to form a combined solution which is rendered oxygen-free. Preferably, this is achieved by bubbling an inert gas (e.g., nitrogen or argon) through the combined solution. Alternatively, the first and second solutions can individually be contacted with the inert gas to render the individual solutions oxygen-free, thereby ultimately forming an oxygen-free combined solution. The combined solution is then stirred in an inert atmosphere until the DHI intermediate is substantially completely formed. The combined solution is preferably stirred for about 30 minutes to about 2 hours to complete the reaction. The progress of the reaction can be monitored by TLC or HPLC.

It is critically important to the invention that the combined solution is rendered oxygen-free and that the aforementioned stirring step is carried out in an inert atmosphere. Otherwise, if the formed DHI is exposed to oxygen, it will polymerize. Consequently, the yield of DAI will be substantially decreased and, potentially, DAI will not be formed at all. The inert atmosphere of the stirring step can be achieved by any known method for creating inert atmospheres. For example, any of the industrially utilized laboratory valve control systems is suitable in the present invention.

Although the process of the present invention works well at room temperatures, it was found to be advantageous to raise the temperature of the combined solution to about 30° C. to about 70° C., preferably about 40° C. to about 50° C., to increase the solubilization rate of dopa. This results in higher yields of DHI (and consequently DAI) than when the reaction is performed at ambient temperature. The preferred temperature range can be achieved by raising the temperature of the combined solution after the first and second solutions have been mixed or, alternatively, the temperature of the first and/or second solution can be individually raised to a higher temperature before the two solutions are combined to give the combined solution the preferred raised temperature range.

Next, a derivatizing agent, such as an acetylating agent, is added to the combined solution, preferably at room temperature. Any acetylating agent can be used in accordance with this invention, including those selected from the group consisting of acetic anhydride and acetyl chloride. The amount of acetylating agent used should be effective to acetylate substantially all of the DHI. This generally requires about 2 to about 3 molar equivalents of the acetylating agent, as compared to the molar amount of dopa present in the first solution.

A base is also added to the combined solution, preferably at room temperature, to form a final solution. The base catalyzes the acetylation of DHI to DAI. Any base can be used in accordance with this invention including those selected from the group consisting of alkyl amine, hydroxyalkyl amine, triethanolamine, pyridine, 4-pyrrolidinopyridine and dimethylaminopyridine. The amount of base used should be sufficient to catalyze the reaction of substantially all of the DHI to DAI. This generally requires about 0.05 to about 0.2 molar equivalents of the catalyst, as compared to the molar amount of dopa present in the first solution. A sequential addition of the derivatizing agent, followed by the base, is preferred, but is not critical. Simultaneous addition is also quite suitable.

The final solution is then stirred until substantially all of the DHI is consumed by the reaction. In general, the final solution should be stirred for about 20–30 minutes.

DAI is then precipitated by cooling the final solution by any method known in the art, and the precipitated DAI may be isolated by any method known in the art. Filtration is the preferred method for isolating DAI. The yield of DAI using this method is unexpectedly high (usually about 50%). The absence of a DAI purification step from this method makes the high yield of DAI even more surprising.

By selecting other indole precursors or other derivatizing agents, the method of this invention can be used to produce other substituted indole derivatives, such as 5,6-dimethoxyindole or 5,6-methylenedioxyindole.

The following examples are given to further illustrate the present invention. It should be understood, however, that the invention is not limited thereto.

EXAMPLE 1

In an inert atmosphere, 7.8 mmol of dopa were combined with 7.8 mmol of c-hydrochloric acid and 45 ml of water to form a first solution. The temperature of this solution was raised to between 40° C. and 50° C. A second solution of 27.9 mmol potassium ferricyanide, 53 mmol sodium bicarbonate, and 45 ml water was added to the first solution. The two solutions were combined as fast as possible and nitrogen gas was bubbled through the solution to remove oxygen therefrom. The combined solution was then rapidly stirred in an inert atmosphere at the raised temperature for 30 minutes, and stirred at ambient temperature for an additional 30 minutes. 20 mmol of acetic anhydride and 15.6 mmol triethanolamine were added to the solution. The solution was stirred for 20 minutes. DAI was precipitated from the solution by cooling the solution in an ice water bath. The DAI precipitate was isolated by filtration. Surprisingly, the method of this invention allowed direct isolation of DAI in a high yield (about 51%), with no purification step. The DAI obtained was characterized using Proton Nuclear Magnetic Resonance (300 MHz, DMSO-$d_e$) and the following readings were obtained: 2.24(s,6H); 6.42(s, 1H); 7.22(s, 1H); 7.32(s, 1H); 7.39(m, 1H); 11.22(s, 1H). The melting point of the DAI obtained is 130°–131° C.

EXAMPLE 2

The process of Example 1 was repeated, except the combined solution was stirred only at ambient temperature for about 30 minutes. The yield of DAI was about 43%.

EXAMPLE 3

A first solution of 5.1 g. of dopa in 25 ml. 1N HCl and 125 ml. of water was placed in a three-necked flask, with a dropping funnel attached. Nitrogen gas was bubbled through the first solution for about 5 minutes to remove oxygen dissolved in the solution. Afterwards, the first solution was kept in an inert (nitrogen) atmosphere and heated to about 45° C. A second solution containing 30.6 g. of $K_3Fe(CN)_6$ and 14.87 g. of $NaHCO_3$ in 150 ml. of water was saturated with nitrogen to remove oxygen therefrom, and placed in the dropping funnel. The second solution was rapidly added to the first solution, while an inert atmosphere was maintained. The combined solution was then stirred at 45°–50° C. in $N_2$-atmosphere for about two hours. Afterwards, the combined solution was allowed to cool. 10 ml. of acetic anhydride and 5 ml. of pyridine were added to the combined solution. The solution was then stirred for about 30 minutes. DAI was precipitated from the solution by cooling the solution in an ice water bath. The DAI precipitate was isolated by filtration. The DAI yield was approximately 50%, with no purification step required.

It will be apparent to those skilled in the art that the invention described herein can be practiced by other than the embodiments disclosed herein, which are presented for the purpose of illustration and not of limitation, and the present invention is limited only by the claims that follow.

We claim:

1. A method of producing and isolating 5,6-diacetoxyindole in a single reaction vessel comprising the following steps:
   (a) preparing a first solution comprising dopa, water and a solubilizing agent selected from the group consisting of an acid having a $pk_a$ value equal to or less than 4 and a first base having a $pk_b$ value equal to or greater than 10;
   (b) preparing a second solution comprising an oxidant, a buffer and water;
   (c) mixing the first and second solutions to form a combined solution which is rendered oxygen-free and has a pH of from about 6 to about 9;
   (d) stirring said combined solution in an inert atmosphere until 5,6-dihydroxyindole is substantially completely formed;
   (e) adding a derivatizing agent and a second base to said combined solution to form a final solution, wherein said derivatizing agent is present in an amount to derivatize substantially all of said 5,6-dihydroxyindole;
   (f) stirring said final solution until said 5,6-dihydroxyindole is substantially fully consumed;
   (g) cooling said final solution to precipitate 5,6-diacetoxyindole;
   (h) isolating the precipitated 5,6-diacetoxyindole.

2. The method of claim 1 wherein said combined solution is rendered oxygen-free by contacting an inert gas therewith.

3. The method of claim 1 wherein said combined solution is rendered oxygen-free by individually contacting said first solution and said second solution with an inert gas.

4. The method of claim 1 further comprising raising the temperature of said combined solution to about 30° C. to about 70° C.

5. The method of claim 1 further comprising raising the temperature of said first solution to about 30° C. to about 70° C.

6. The method of claim 5 further comprising raising the temperature of said second solution to about 30° C. to about 70° C.

7. The method of claim 1 wherein said second base and said derivatizing agent are added simultaneously.

8. The method of claim 1 wherein said second base and said derivatizing agent are added sequentially.

9. The method of claim 1 wherein the molar amount of the solubilizing agent is at least equivalent to the molar amount of dopa.

10. The method of claim 1 wherein the solubilizing agent is selected from the group consisting of hydrochloric acid, phosphoric acid, sodium hydroxide and potassium hydroxide.

11. The method of claim 4 wherein the temperature of the combined solution is raised to about 40° C. to about 50° C.

12. The method of claim 1 wherein the oxidant is selected from the group consisting of potassium ferricyanide, sodium ferricyanide and ammonium ferricyanide.

13. The method of claim 1 wherein the oxidant is present in an amount sufficient to convert substantially all of the dopa to 5,6-dihydroxyindole.

14. The method of claim 1 wherein the buffer is selected from the group consisting of sodium bicarbonate, potassium bicarbonate, phosphate, borate and amine-containing compounds.

15. The method of claim 4 wherein the combined solution is stirred at the raised temperature for about 30 minutes.

16. The method of claim 15 wherein the combined solution is stirred at ambient temperature for about an additional 30 minutes.

17. The method of claim 1 wherein the derivatizing agent is selected from the group consisting of acetic anhydride and acetyl chloride.

18. The method of claim 1 wherein the second base is an amine base.

19. The method of claim 1 wherein the final solution is stirred for about 20 minutes.

20. The method of claim 13 wherein the amount of oxidant is about 3 to about 4 molar equivalents of dopa.

* * * * *